United States Patent [19]
Schaefer

[11] Patent Number: 5,792,048
[45] Date of Patent: Aug. 11, 1998

[54] INDENTIFICATION PILL WITH INTEGRATED MICROCHIP: SMARTPILL, SMARTPILL WITH INTEGRATED MICROCHIP AND MICROPROCESSOR FOR MEDICAL ANALYSES AND A SMARTPILL, SMARTBOX, SMARTPLAGUE, SMARTBADGE OR SMARTPLATE FOR LUGGAGE CONTROL ON COMMERCIAL AIRLINERS

[76] Inventor: Guenter Schaefer, 209 N. Atlantic Blvd., #6C, Ft. Lauderdale, Fla. 33304

[21] Appl. No.: 707,015

[22] Filed: Sep. 3, 1996

[51] Int. Cl.⁶ .................................................. A61B 5/00
[52] U.S. Cl. ........................ 600/302; 235/380; 235/487
[58] Field of Search ........................... 235/380, 487; 600/302

[56] References Cited

U.S. PATENT DOCUMENTS 3,719,183  3/1973  Schwartz .................. 600/302

*Primary Examiner*—Harold Pitts
*Attorney, Agent, or Firm*—Ronald V. Davidge

[57] ABSTRACT

A capsule, which is resistant to stomach acids, is shaped like a medical pill, and can be orally taken in the same manner. This capsule includes a pair of plastic shells surrounding a circuit board, and, in an alternative embodiment, a microprocessor. The circuit board includes memory circuits for storing personal identification data, which is made available when needed, but which cannot be changed without a code number or word. A battery, an antenna for wireless access, and a metal disk supporting the location of the capsule with metal detectors may be added. A device with such additional features can also be used to identify luggage, to be transported on commercial airliners, as belonging to the holder of the ticket and/or boarding card.

15 Claims, 6 Drawing Sheets

5,792,048

INDENTIFICATION PILL WITH INTEGRATED MICROCHIP: SMARTPILL, SMARTPILL WITH INTEGRATED MICROCHIP AND MICROPROCESSOR FOR MEDICAL ANALYSES AND A SMARTPILL, SMARTBOX, SMARTPLAGUE, SMARTBADGE OR SMARTPLATE FOR LUGGAGE CONTROL ON COMMERCIAL AIRLINERS

BACKGROUND OF THE INVENTION

Catastrophic transportation accidents, such as airline crashes, are often accompanied by massive destruction including the effects of explosions and fire, making the identification of all of the accident victims very difficult or even impossible. Such identifications, if they can be made, are sometimes based on the examination of small pieces of evidence, such as a fragment of skin with a partial tattoo, a trace of a prescription drug, or a tooth with a filling. In this regard, Dr. Jack Frost, Vice President of the National Association of Medical Examiners, has said that: "The ideal outcome would be to find something to identify everyone on the aircraft so there are no lingering questions."

What is needed is an identification instrument within the body, ideally in the stomach, which can be orally taken at the beginning of a journey.

SUMMARY OF THE INVENTION

A first objective of this invention is to provide an identification pill to be used by travelers, which has an integrated microchip with data storage capability, with read and write capability, and a built-in security code that does not allow data to be changed, except by the owner of the information.

A second objective of this invention is to provide an identification pill which can be orally taken and which is resistant against all aggressive body fluids.

A third objective of this invention is to provide an identification pill which leaves the body after a normal digestion period, and which is harmless to use.

A fourth objective of this invention is to provide a device which can be implanted into tissue or muscle for a long-term application.

A fifth objective of this invention is to provide an implantable or ingestible capsule which includes data storage capabilities and an integral microprocessor.

A sixth objective of this invention is to provide an implantable or ingestible capsule which can include an integral battery.

A seventh objective of this invention is to provide a system including an implantable or ingestible capsule having internal data storage and an external device writing data to this data storage and reading data therefrom, with an interface between the implantable or ingestible capsule including a number of holes in the implantable or ingestible capsule through which pins from the external device extend to contact tabs within the implantable or ingestible capsule, and with these holes being sealed in the absence of the pins.

An eighth objective of this invention is to provide an ingestible capsule to which analyzing subsystems may be added for medical monitoring, with the device staying in the stomach for about 24 hours.

A ninth objective of this invention is to provide an implantable device which can be used to dispense medication over an extended period.

A tenth objective of the invention is to provide an ingestible or implantable device including an internal antenna, having an ability to vary processes performed by the device in response to radio signals.

An eleventh objective of the invention is to provide a miniature device including processing and radio communications capability for security applications. For example, such a device, fastened inside each piece of the luggage of an airline traveler, can electronically tie the luggage to an individual airline ticket or boarding card at baggage check in.

DETAILED DESCRIPTION

Figure 1:
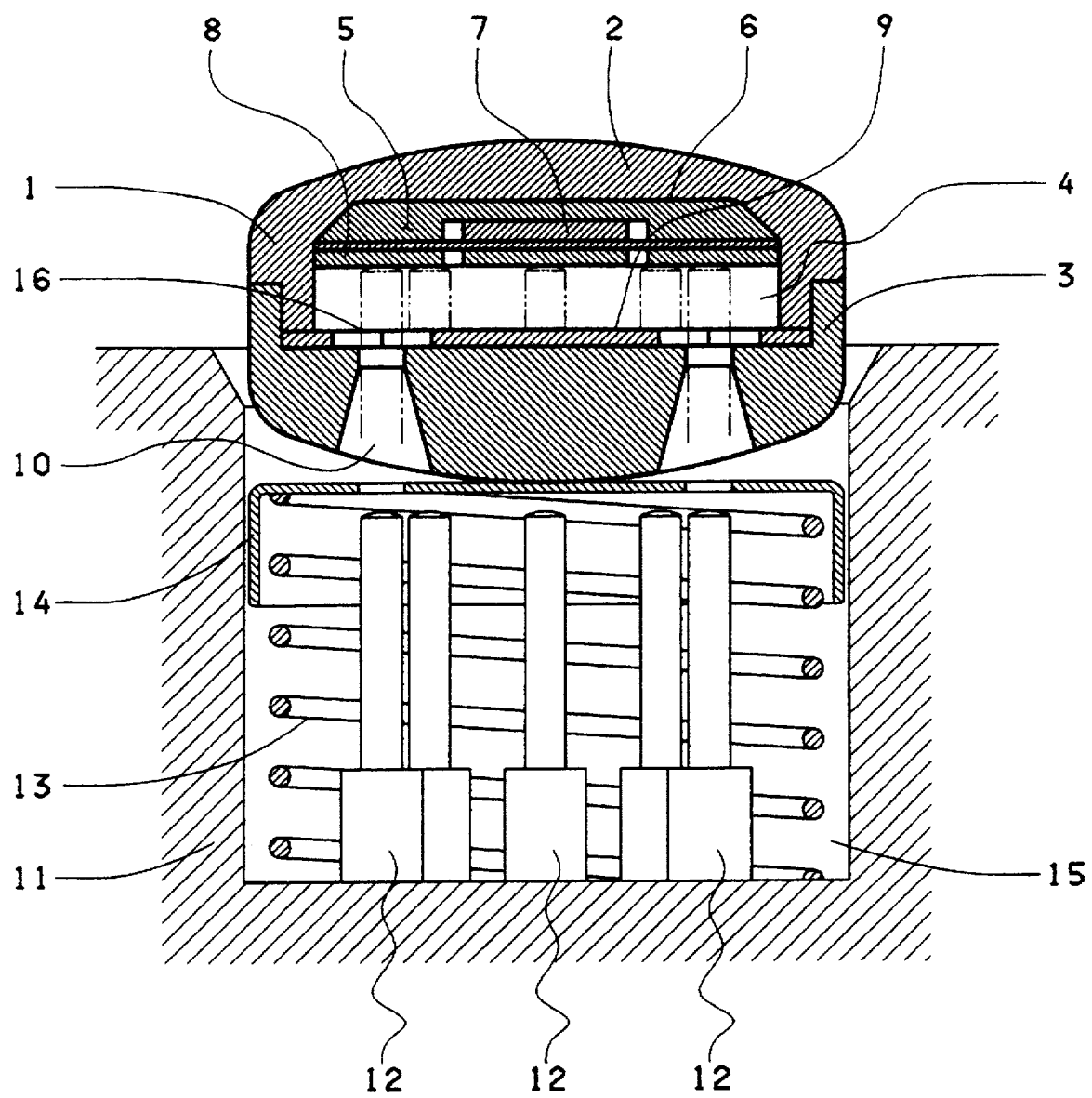
FIG. 1 is a longitudinal cross-sectional view of an ingestible identification pill built in accordance with the present invention.

FIG. 1 is a longitudinal cross-sectional view of an ingestible capsule 1, built in accordance with the present invention, within a device cavity providing electrical contact pins used for writing data into the ingestible capsule 1 and for reading data therefrom. This ingestible capsule 1 includes two acid-resistant plastic shells 2, 3. The upper plastic shell 2 has a shaped cavity 4 accommodating a plastic disc 5, which has on one side a metallic surface 6 that allows metal detectors to locate the ingestible capsule. The disk 5 is otherwise composed of an insulating plastic material.

A circuit chip 7, adapting to the shape of the identification pill 1, is embedded inside a small cavity of the plastic disc 5, which also acts as a carrier of contact tabs 8 attached to the circuit chip 7. The shaped cavity 4 is sealed by a plastic membrane 9, which can be penetrated by contact pins 12. After the retraction of the contact pins 12, the plastic membrane 9 seals itself and protects the circuit chip 7 with its contact tabs 8.

The lower plastic shell 3 is constructed with tapered penetration holes 10 which lead to the contact tabs 8. The lower plastic shell 3 is sealed to the upper plastic shell 2, holding the plastic membrane 8 in place. In the example of FIG. 1, the ingestible capsule 1 is shown with contact pins 12, extending upward within a cavity 15 of an external device 11, entering the tapered penetration holes 10. The ingestible capsule 1 is next pushed down over the contact pins 12, so that the contact pins 12 are brought into contact with contact pads 8. Data can then be read from, or written to, memory circuits within the ingestible capsule 1 through the contact pins 12. As the ingestible capsule 1 is pushed into the cavity 15, a carrier 14 is depressed, compressing a spring 13.

Figure 2:
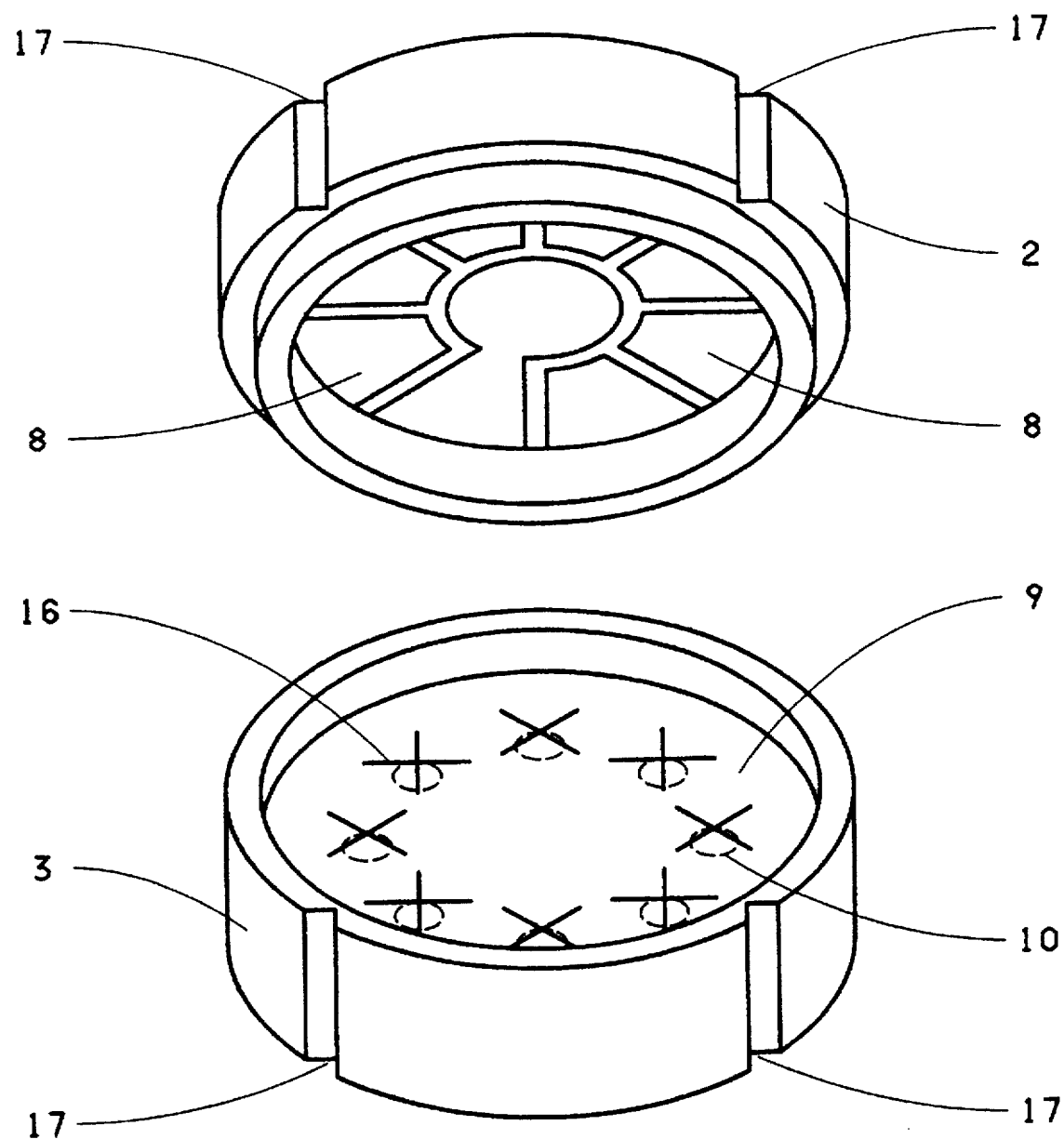
FIG. 2 is an isometric view of the ingestible identification pill of FIG. 1 in an opened condition.

FIG. 2 is an isometric view of the ingestible capsule 1 of FIG. 1 in an opened condition, exposing the contact tabs 8 of the circuit chip 7. The upper and lower plastic shells 2, 3 are key coded by features 17 to ensure positioning of all contact tabs 8 relative to penetration holes 10. The penetration holes 10 for the contact pins 12 (shown in FIG. 1) are sealed by the plastic membrane 9. To facilitate penetration, the plastic membrane 9 can have When the contact pins 12 are removed, the flaps formed between the cross-cuts 16 return to their flattened condition, restoring the seal established using the plastic membrane 9.

When the ingestible capsule 1 is orally taken at the beginning journey it serves as an identification tablet, which is protected against heavy impacts and fire, which cannot be lost, and which provides identification data that can be recovered.

The circuit chip preferably includes a built in security code without which stored data cannot be changed.

Figure 3:
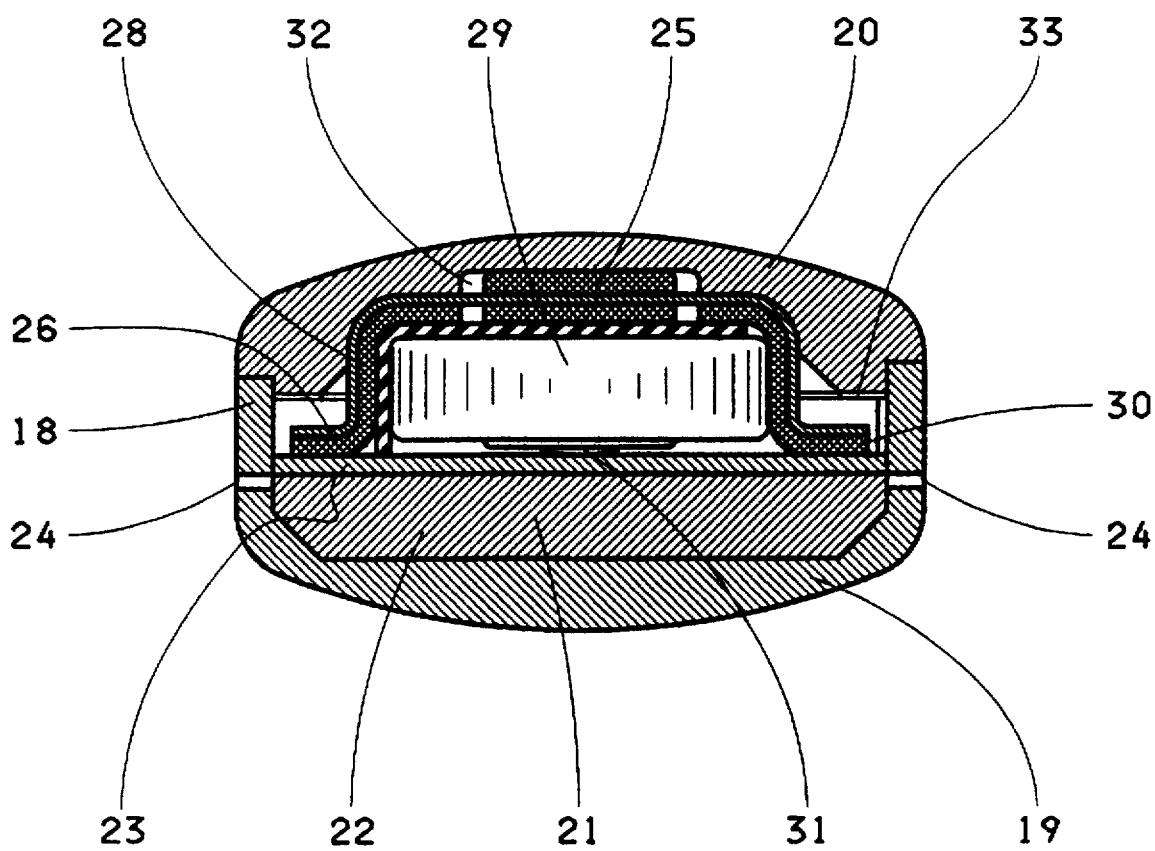
FIG. 3 is a longitudinal cross-sectional view of a miniature device built in accordance with a second version of the present invention, including a battery for powering mechanical devices needed in applications such as analysis.

FIG. 3 is a longitudinal cross-sectional view of a miniature device 18 built in accordance with a second version of the present invention, which is enclosed by two acid-resistant plastic shells 19, 20. The lower plastic shell 19 has a cavity 21 in which a circuit board 22 is inserted. The circuit board accommodates micro mechanics, such as a combination of pumps, sensors, counters, motors, and other miniature devices (not shown) which support analytic instrumentation. The circuit board 22 is constructed with contact tabs 23 that engage the contact tabs 26, 30, 31 of a circuit chip with an integrated microprocessor 25. Certain contact tabs 23 also engage the contact surfaces of the battery 29. The circuit board may also include a reservoir for the storage of medicine caused to be measured and delivered by means of a pump and motor, at intervals as required, by programming the integrated microprocessor 25. Contacts to a device external to the miniature device 18 are made through holes or contacts 24, which are accommodated in the lower plastic shell 19. The molded cavity 32 of the upper plastic shell 20 is shaped to accommodate the microprocessor 25. The contact tabs 26, 30 of the microprocessor 25 are bent in such a way that a battery 29 with an insulating shell 28 can be accommodated, achieving power distribution to both the circuit board 22 and the microprocessor 25.

Adding an antenna 33 to the rim of the upper plastic shell 20 provides for two-way wireless communication, enabling an external device to call up the results of a process, and enabling an external device to transmit new instructions. This capability provides the miniature device 18 with an advantage of flexibility. The plastic shells 19, 20 are sealed at assembly. The miniature device 18 is also suitable for implantation into tissue or muscle. Miniature devices 18 for implantation can also be manufactured from suitable metals.

Figure 4:
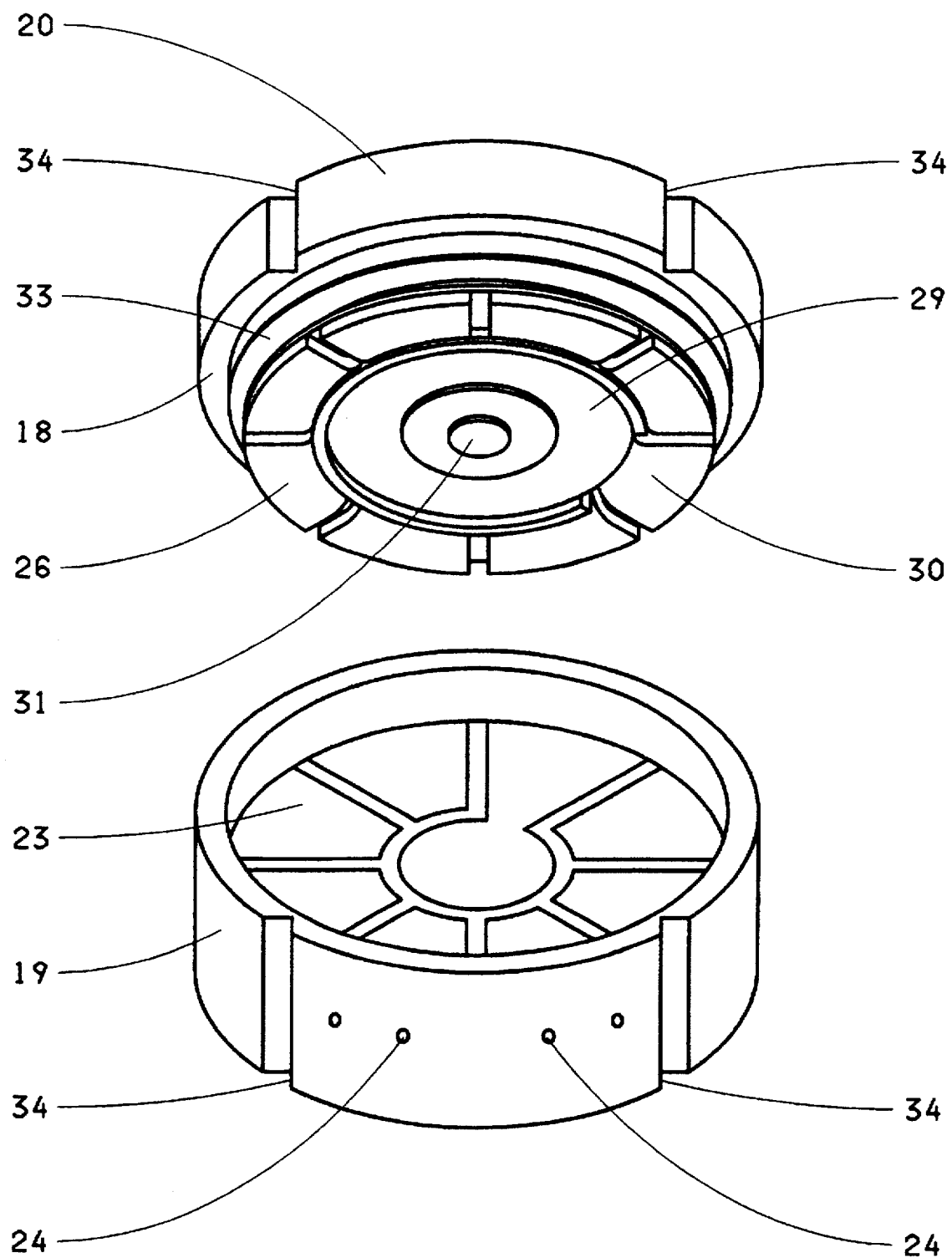
FIG. 4 is an isometric view of miniature device of FIG. 3.

FIG. 4 is an isometric view of the miniature device 18 of FIG. 3 in an opened condition. Plastic shells 19, 20 are coded by features 34 so that the relative positioning of the contact tabs 23, 26, 30, 31 is ensured. The position of the antenna 33, as well as that of the battery 29, are shown within the opened upper plastic shell 20. The contact tabs 23 of the circuit board 22 are shown within the opened lower plastic shell 19.

To increase safety against terrorism on airliners, the miniature device 18 can also be used to identify luggage, establishing a relationship between the luggage and the holder of a ticket and/or boarding card. In this application, a miniature device 18 with two-way radio communication capability is non-removably attached to the inside of each piece of the traveller's luggage. When the luggage is checked at the airport, each piece of luggage is tied to the ticket and/or boarding card, for example, by printing a bar code that contains this information onto the ticket and/or boarding card. The luggage is then put into a waiting stage, such as a circulating conveyer belt. After the owner of the luggage has checked in with the ticket and/or boarding card being passed through an electronic reader and entered the airliner, the luggage is cleared, so that it can be loaded onto the airliner. The traveler cannot be allowed to leave the airliner after this procedure. On the other hand, should a traveler request or try to leave the airliner, his luggage can be swiftly located. When a traveler changes from one airliner to another, his luggage can be checked through to the connecting airliner by transporting the luggage to the waiting stage for luggage of the connecting flight. This process prevents anyone from checking unaccompanied luggage onto a flight, reducing the threat of sabotage.

Figure 5:
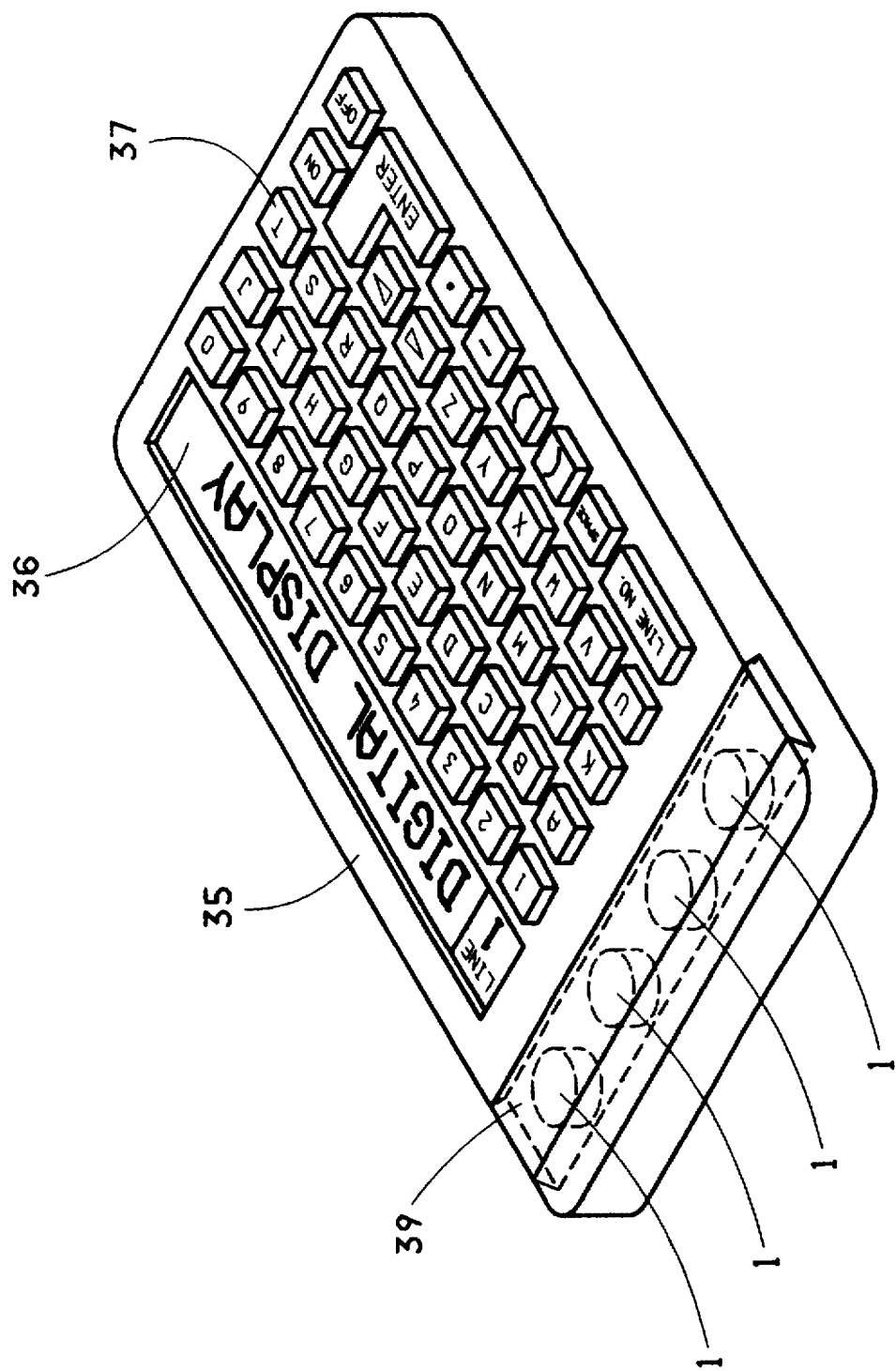
FIG. 5 is an isometric view of a stand-alone device for reading and writing data to the identification pill of FIG. 1.

FIG. 5 is an isometric view of a stand-alone device 35 for reading and writing data to and from the identification pill of FIG. 1. This stand-alone device 35 includes a digital display 36 and a keyboard 37. This stand-alone device 35 includes a number of cavities 15 having contact pins 12, as described above in reference to FIG. 1. When a cover 39 of the stand-alone device 35 is in the closed position shown in FIG. 5, the ingestible capsules 1 are pushed down to achieve contact with the contact pins 12. When the cover 39 is removed, the ingestible capsules 1 can be taken off the cavities 15 (shown in FIG. 1).

Figure 6:
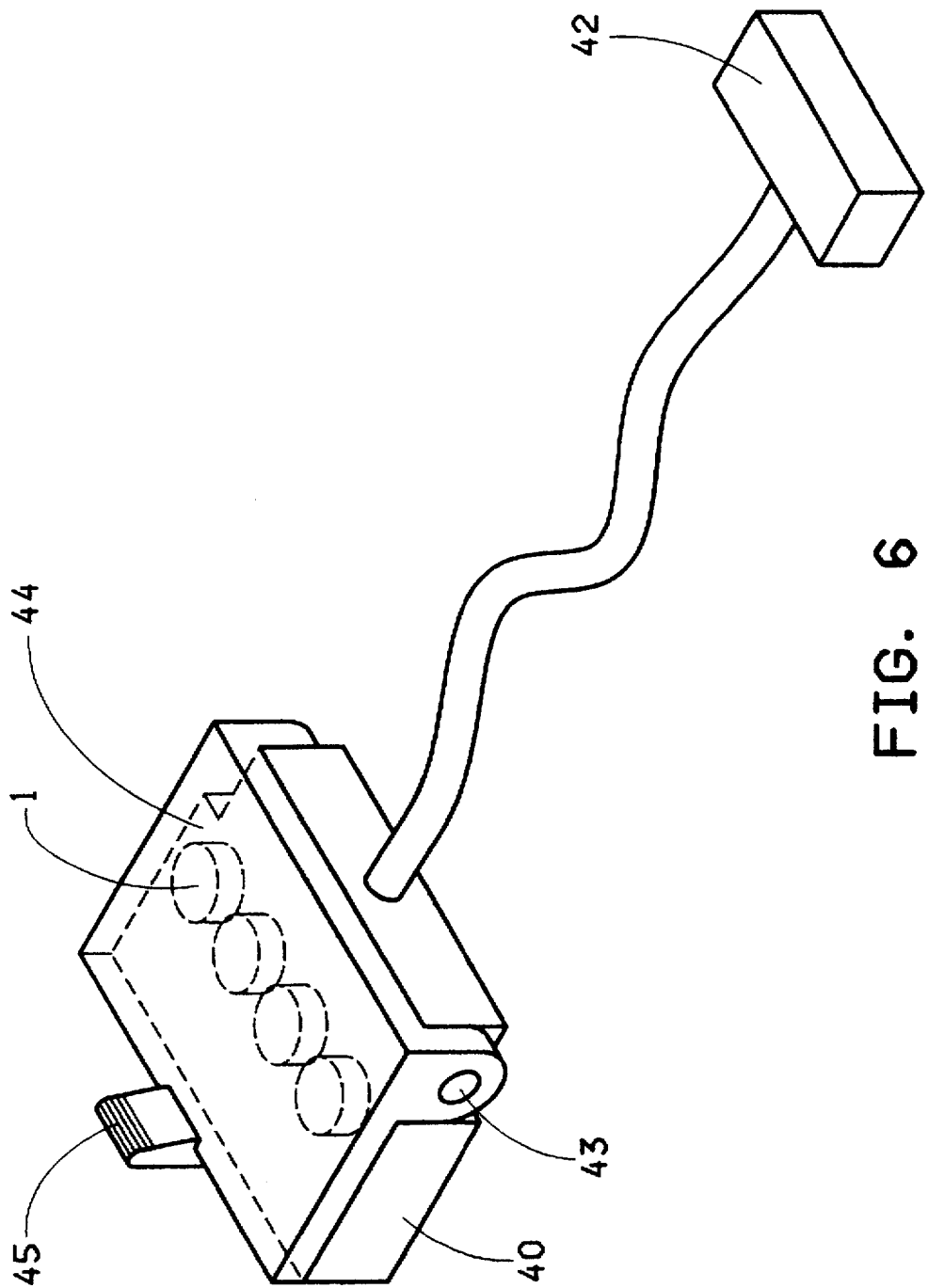
FIG. 6 is an isometric view of a peripheral unit for reading and writing data to the identification pill of FIG. 1 by means of software executing in a computing system.

FIG. 6 is an isometric view of a computer peripheral device 40, which can read data from the ingestible capsule 1, and write data thereto, in accordance with a software program executing in an external computer (not shown). The computer peripheral device 40 has integrated cavities 15, which are equipped with contact pins 12, as described above, in reference to FIG. 1. A cover 44, hinged on pins 43, holds a number of ingestible capsules 1 in contact with the contact pins 12 (shown in FIG. 1). When a snap 45 is released, the hinged cover 44 can be opened so that ingestible capsules 1 can be inserted or removed. The connector 41 is plugged to a computer (not shown)

I claim as my invention:

1. A capsule comprising:

an upper shell;

a lower shell having a plurality of penetration holes extending therethrough, and a periphery sealed to said upper shell;

a circuit board between said upper and lower shells, having a plurality of data storage devices;

a plurality of conductive contact surfaces, with each contact surface within said plurality thereof extending adjacent a penetration hole in said plurality thereof, wherein said contact surfaces are connected to said data storage devices in a manner allowing data to written to said data storage devices and read therefrom through said contact surfaces; and a penetrable sealing member extending between said plurality of penetration holes in said lower shell and said plurality of contact surfaces.

2. The capsule of claim 1, wherein said upper and lower shells are of a size and shape allowing said capsule to be swallowed, and said upper and lower shells are composed of materials resistant to stomach acids.

3. The capsule of claim 1, additionally comprising a partially metallic member facilitating location of said capsule by means of a metal detector.

4. The capsule of claim 1, wherein said penetrable sealing member is composed of a flexible plastic material having a slit adjacent each said penetration hole, with said slit opening when a pin is pushed through said penetration hole and closing when said pin is removed from contact with said penetrable sealing member.

5. Apparatus comprising:

A capsule including
- an upper shell,
- a lower shell having a plurality of penetration holes extending therethrough, and a periphery sealed to said upper shell,
- a circuit board between said upper and lower shells, having a plurality of data storage devices,
- a plurality of conductive contact surfaces, with each contact surface within said plurality thereof extending adjacent a penetration hole in said plurality thereof, wherein said contact surfaces are connected to said data storage devices in a manner allowing data to written to said data storage devices and read therefrom through said contact surfaces, and
- a penetrable sealing member extending between said plurality of penetration holes in said lower shell and said plurality of contact surfaces; and a data transfer device, external to said capsule, including
- a capsule holder including a cavity for holding said capsule, with alignment surfaces surrounding said cavity to engage and align said capsule therein, and
- a plurality of contact pins extending within said cavity and through said penetration holes to engage conductive contact surfaces within said plurality thereof.

6. The apparatus of claim 5, wherein said upper and lower shells are of a size and shape allowing said capsule to be swallowed, and said upper and lower shells are composed of materials resistant to stomach acids.

7. The apparatus of claim 6, with said capsule additionally including a partially metallic member facilitating location of said capsule by means of a metal detector.

8. The apparatus of claim 5, wherein said penetrable sealing member is composed of a flexible plastic material having a slit adjacent each said penetration hole, with said slit opening when a contact pin within said plurality thereof is pushed through said penetration hole and closing when said contact pin is removed from contact with said penetrable sealing member.

9. The apparatus of claim 5, with said data transfer device additionally including, within said cavity,
- a carrier moving downward under said capsule as said capsule is moved downward on said contact pins, and
- a spring compressed by downward movement of said carrier, with releasing said capsule within said cavity causing said spring to move said carrier and said capsule upward.

10. The apparatus of claim 5, wherein said data transfer device causes data to be written to said data storage devices of said capsule through said contact pins, when said contact surfaces are held in contact with said contact pins.

11. The apparatus of claim 10, wherein said data transfer device additionally causes data to read from said data storage devices of aid capsule through said contact pins, when said contact surfaces are held in contact with said contact pins.

12. The apparatus of claim 10, with said data transfer device additionally including a door movable between a first position, in which said capsule can be loaded into said cavity and removed therefrom, and a second position, in which said door holds said contact surfaces of said capsule in contact with said contact pins of said data transfer device.

13. The apparatus of claim 10, in which said data transfer device includes a keyboard and a digital read-out.

14. The apparatus of claim 10, in which said data transfer device includes a connection for attachment to a computing system.

15. The apparatus of claim 10, in which data is written to said data storage devices in response to selection of an encoded number sequence.

* * * * *